United States Patent [19]

Loch

[11] 4,027,238

[45] May 31, 1977

[54] METHOD AND APPARATUS FOR THE MOISTURE MEASUREMENT OF FLAT STRUCTURES, ESPECIALLY TEXTILE WEBS

[75] Inventor: Ernst Loch, Uster, Switzerland

[73] Assignee: Zellweger Uster Ltd., Uster, Switzerland

[22] Filed: Aug. 16, 1976

[21] Appl. No.: 714,857

[30] Foreign Application Priority Data

Oct. 20, 1975 Switzerland ............... 13570/75

[52] U.S. Cl. ............................. 324/65 R; 73/73
[51] Int. Cl.² .............................. G01N 27/12
[58] Field of Search ............ 73/73, 159; 162/263; 324/65 R, 61 R, 61 P

[56] References Cited

UNITED STATES PATENTS

| | | | |
|---|---|---|---|
| 2,484,594 | 10/1949 | Spangenberg | 324/65 R X |
| 2,942,352 | 6/1960 | Eicken | 324/65 R X |
| 3,384,815 | 5/1968 | Lyall et al. | 324/65 R |

FOREIGN PATENTS OR APPLICATIONS 338,170  6/1959  Switzerland ............... 73/73

*Primary Examiner*—Jerry W. Myracle
*Attorney, Agent, or Firm*—Werner W. Kleeman

[57] ABSTRACT

A method of, and apparatus for, measuring the moisture content of flat textile structures, especially textile webs, wherein there are produced, by virtue of the measuring operation, useful signal components of the same polarity dependent upon the conductance of the test material. There are produced disturbance signal components of opposite polarity dependent upon external voltages. And the useful signal components are additively processed into a measurement value, whereas the disturbance signal components, by addition thereof, due to their opposite polarity, at least approximately eliminate one another.

11 Claims, 7 Drawing Figures

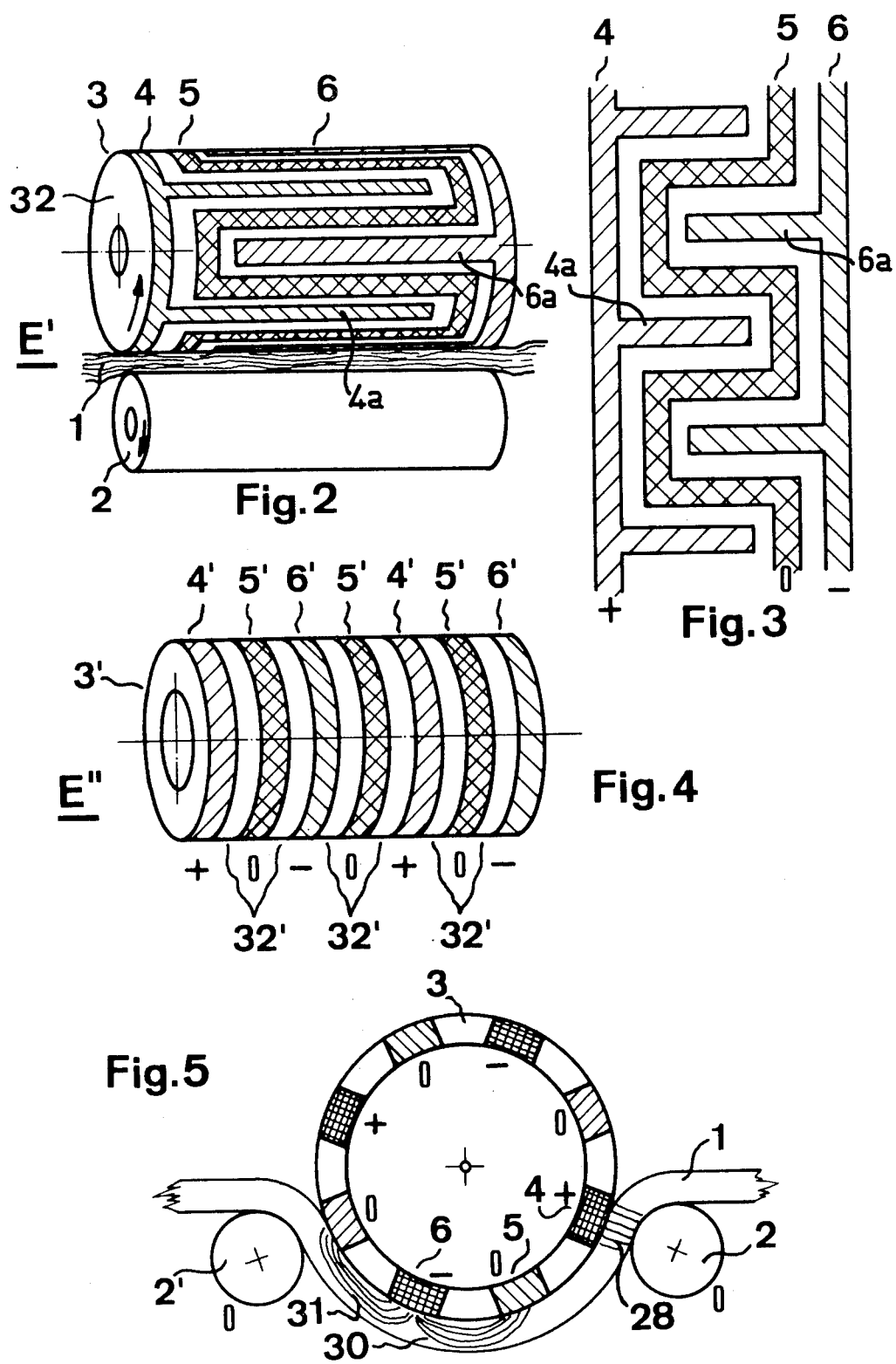

METHOD AND APPARATUS FOR THE MOISTURE MEASUREMENT OF FLAT STRUCTURES, ESPECIALLY TEXTILE WEBS

BACKGROUND OF THE INVENTION

The present invention relates to a new and improved method of, and apparatus for, measuring the moisture content of flat structures, especially textile webs.

The textile moisture regulators heretofore known carrying out a moisture measurement according to the conductance-measurement principle, have only been able to fulfill their function to a limited extent, especially when there are used synthetic textile fibers. Thus, the conventional input circuit, formed by a voltage divider, the oftentimes extremely high current-flow resistance of the textile web to be measured and a limited high ohmic fixed resistor, no longer can furnish any practically usable signal evaluation with divider ratios from approximately 1:100 and 100:1.

The usual resistance values up to about $10^{12}$ ohms for synthetic or man-made textiles lead to voltage divider ratios which are greater by several decades than the indicated values. Also a corresponding increase of the fixed resistor of the mentioned voltage divider, as a general rule, is hardly realizable due to the limited insulation properties of the insulation material which comes into use and the input resistance of the required measuring amplifier.

Apart from such limitations of the measuring range there also exist disturbance effects due to external voltages, such as for instance those emanating from the extreme high-ohmic properties of the test material and the input circuit of the measuring apparatus and the introduction of noise or hum brought about by the practically required length of the measuring conductors as well as falsification of the measuring signal by fault currents caused by the high static charge which normally is produced at moved textile webs. These fault currents are often of the same order of magnitude or, in fact, even larger than those measuring currents of several picoamperes conventional for dry synthetic textiles, and accordingly, render impossible a reliable measurement of such materials.

SUMMARY OF THE INVENTION

Hence, it is a primary object of the present invention to provide a new and improved method of measuring the moisture or dampness of flat textile structures, especially textile webs, and an apparatus for the performance of the aforesaid method, by means of which there can be avoided or, at least reduced in their effect, disturbing influences impairing the possible measuring range and the measuring reliability.

The method aspects of the present invention for measuring the moisture content of test material, such as flat textile structures, especially textile webs, is manifested by the features that there are derived, by virtue of the measuring operation, useful signal components of the same polarity dependent upon the conductivity or conductance of the test material, there are derived disturbance signal components of opposite polarity which are dependent upon external voltages, the useful signal components are additively processed into a measurement value, and the disturbance signal components, by addition, at least approximately eliminate one another due to their opposite polarity.

The invention also relates to apparatus for the performance of the aforementioned method aspects, and such apparatus comprises an electrode arrangement which comes into contact with the test material. The electrode arrangement has at least one ground electrode, at least one further electrode at positive potential and at least one further electrode at negative potential. The electrode carrying the positive potential is connected with a first input and the electrode carrying the negative potential with a second input of an amplifier arrangement having two direct-current series connected partial amplifiers.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 2 illustrates a construction of electrode arrangement;

FIG. 3 is a development of an electrode arrangement according to FIG. 2;

FIG. 4 is a further construction of the electrode arrangement;

FIG. 5 is a cross-sectional view through the arrangement of FIG. 2;

DETAILED DESCRIPTION OF THE PREFERRED EMBODIMENTS

Figure 1:
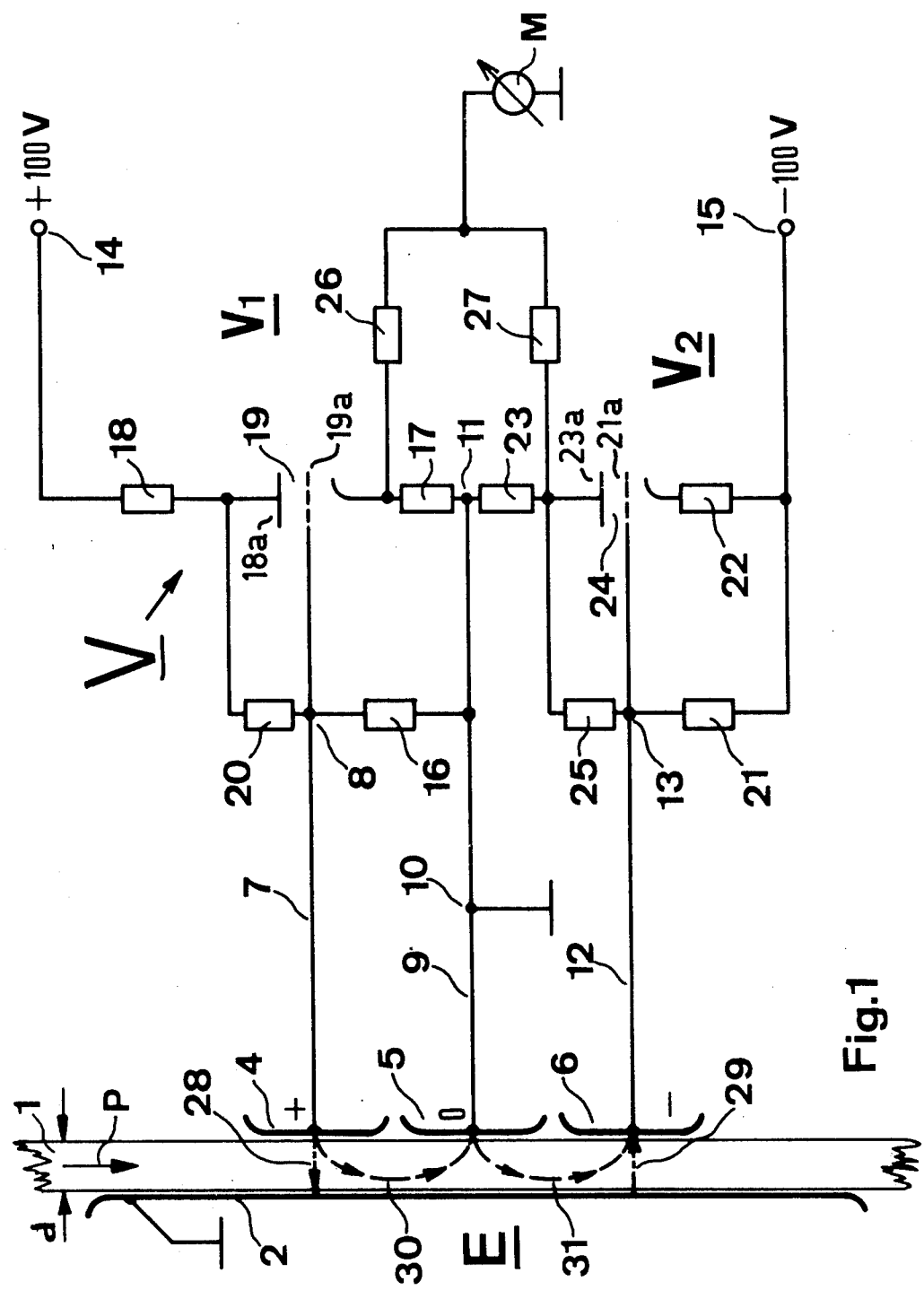
FIG. 1 schematically illustrates an apparatus for explaining the principle of operation of the present invention, not drawn to scale.

Describing now the drawings, it is to be understood that throughout the various Figures there have been generally used the same characters to denote identical or analogous components. Also the drawings have not been drawn to scale. In FIG. 1, for the purpose of explaining the operation of the invention, there is schematically shown an apparatus according to the invention wherein the flat or band-shaped test material 1 of a thickness $d$, for instance a textile web, passes through an electrode arrangement E. The test material 1 thereby contacts with its one surface a first electrode 2 connected with ground or earth, i.e. thus carrying zero potential, and with its opposite surface the test material 1 contacts a series of further electrodes 4, 5 and 6. As to these further electrodes 4, 5 and 6, the electrode 4 has delivered thereto, via the conductor or line 7, a positive potential, the electrode 5 has delivered thereto, via the line 9 from the ground point 10, zero potential, and the electrode 6 has delivered thereto, via the line or conductor 12, a negative potential.

The line or conductor 7 leads from the further electrode 4 to a first input 8 of an amplifier arrangement V. A line or conductor 9 leads from the further electrode 5 via the ground terminal 10 to a center tap or point 11 of the amplifier arrangement V. A line or conductor 12 leads from the further electrode 6 to a second input 13 of the amplifier arrangement V.

The amplifier arrangement V is manifested by the features that it posseses two direct-current series connected partial amplifiers $V_1$, $V_2$. At a terminal 14 there is delivered to the amplifier arrangement V a positive supply voltage, for instance +100 volts and at a terminal 15 a negative supply voltage, for instance −100 volts. For instance, the amplifier arrangement V, as illustrated in FIG. 1, can be designed as a tube amplifier, but it is however also possible to select a semiconductor-amplifier construction, preferably one having a field-effect transistor input. Of course, in such case there are to be selected suitable supply voltages as is conventional.

With the amplifier arrangement V the partial amplifier $V_1$ possesses a grid resistor 16, a cathode resistor 17, an anode resistor 18 and a feedback resistor 20 which is located between the anode 18a and grid 19a of the amplifier tube 19. In analogous manner the partial resistor $V_2$ possesses a grid resistor 21, a cathode resistor 22, an anode resistor 23 and a feedback resistor 25 located between the anode 23a and grid 21a of the amplifier tube 24.

The output signal of the partial amplifier $V_1$ and the output signal of the partial amplifier $V_2$ are delivered through the agency of a respective resistor 26 and 27 to a measuring element M. This measuring element M thus has delivered thereto the sum of both output signals. The measuring element M also can be combined with a regulation element or itself constructed as a regulation element or it can be a known regulation device arranged following the amplifier arrangement V, which has the function of controlling regulation operations for influencing the test material 1 in accordance with the measurement value delivered by the amplifier arrangement V.

Due to the potential applied to the electrode arrangement E there are formed electrical fields in the test material 1 which produce currents flowing between the individual electrodes. These currents and the voltage drops caused thereby are delivered to the amplifier arrangement V for further processing. The magnitude of the currents flowing through the test material 1 depends primarily upon its moisture content, so that the currents prevailing at the electrode arrangement E and the thus resulting voltage drops constitute a measure for the moisture or dampness of the test material 1. In the case of relatively dry test material such is very high-ohmic and there prevail between the individual electrodes of the electrode arrangement E resistance values up to about $10^{12}$ ohms. This high ohm characteristic of the test material causes difficult problems for the measuring operation in that in consequence thereof there can easily arise disturbance voltages which disturb the measuring operation. In particular these are present so-called noise or hum disturbances, emanating from disturbing electrical fields, especially those caused by convential electrical alternating-current installations. Moreover, the test material 1, especially if the same is a textile web formed of synthetic fibers, can be for instance electrostatically charged by friction, specifically to voltage values which are considerably greater than the useful signals resulting from the present measuring arrangement.

By virtue of the measuring arrangement, according to FIG. 1, there is now achieved the result that the measuring signals which are decisive for the moisture of the test material 1 augment one another with respect to the direct-current flow through the amplifier arrangement V and therefore produce an output signal in the measuring element M, whereas the mentioned disturbing influences produce measuring signals which, owing to their control action upon the current flow through the amplifier arrangement V, are oppositely directed and thus extensively eliminate one another.

The invention thus has the decisive advantage that it is not prone to disturbing influences of the aforementioned type and nonetheless possesses a measuring sensitivity which is adequate for the practically extremely high ohm test material. This advantage is achieved in that the electrode arrangement E is a push-pull arrangement and the amplifier arrangement V functions in an additive manner with regard to the measuring signals from the further electrodes 4 and 6, and therefore, the useful signal components which change in the same direction are employed for the indication, whereas the disturbance voltages dependent upon the external voltages and acting in opposed direction at least extensively eliminate one another. Due to the potentials applied to the further electrodes 4, 5 and 6 there is formed an electrical field 28 between the electrode 4 and the electrode 2 which extends transversely through the test material 1 and an electrical field 29 between the electrode 2 and the electode 6 which likewise extends transversely through the test material. Owing to the currents caused by these fields there appear useful signals at the electrodes 4 and 6, constituting a mass for the moisture of the test material 1. These useful signals are delivered via the conductors or lines 7 and 12 to the first input 8 and the second input 13 respectively, of the amplifier arrangement V. It should be readily apparent that owing to the polarities selected in the present measuring arrangement, the useful signals at the electrodes 4 and 6 assist the direct-current flow through the amplifier arrangement V. Owing to the potentials prevailing at the electrodes 4, 5 and 6 there are however also formed the electrical fields 30 and 31 which extend in the lengthwise direction of the test material 1. It should be easily recognized that also by virtue of these fields 30 or 31 useful signals are formed which add to the measuring signals produced by the fields 28 and 29. With the measuring arrangement according to FIG. 1 the test material 1 therefore is measured both in its transverse direction or dimension as well as also in its lengthwise direction or dimension. It is to be observed that the conductivity or conductance of the test material 1 in the direction of the fields 28 and 29 decreases with increasing thickness $d$, but however the conductivity of the test material 1 resulting in the direction of the fields 30 and 31 increases with increasing thickness $d$. By optimumization of the dimensions of the electrode arrangement E it is therefore possible to approximately compensate, at least over a certain range, the influence of the thickness $d$ of the test material upon the measuring value finally delivered by the measuring arrangement. Also this constitutes a considerable advantage of the invention.

There are possible further advantageous physical manifestations of the invention, which will be explained on the basis of further Figures of the drawing hereinafter.

Thus, in FIG. 2 there is shown a construction of electrode arrangement E'. Also, in FIG. 2 the test material has been designated by reference character 1, and reference character 2 designates the ground electrode. There can be provided more than one ground electrode 2. The ground electrode 2 is is constructed as a cylinder mounted to be rotatable about its lengthwise axis, which is rotated in the direction of the arrow and arranged below the test material 1. Above the test material 1 there is arranged a cylinder 3 rotatable about its lengthwise axis in the direction of the arrow, this cylinder 3 consisting of a cylidrical-shaped insulation element 32 and at the jacket surface or shell of which there have been applied the further electrodes 4, 5 and 6, for instance by a galvanic process. The further electrodes 4 and 6 are constructed comb-shaped, offset with respect to one another and extend towards one another. In the intermediate spaces formed between the comb teeth 4a, 6a there is arranged a so-called meander-shaped ground electrode 5.

In order to render clearer the arrangement, there has been illustrated in FIG. 3 a development of the cylinder 3. The individual electrodes 2, 4, 5 and 6 have delivered thereto, in conventional manner, for instance by means of sliding contact or slip rings, the necessary potentials as indicated during the discussion of FIG. 1. Thus, this has not been shown in FIG. 2 to preserve clarity in illustration.

According to the directions of rotation of the cylinder-shaped ground electrode 2 and the cylinder 3, indicated by the arrows, the test material 1 moves from the rear towards the front through the measuring arrangement. It will be recognized that the test material 1 bears at its one surface continually at the ground electrode 2 and with its other surface at the electrodes 4, 5 and 6. Further the test material, prior to entering the narrowest location, is previously contacted by a part of the grounded electrode 5 extending transverse to the direction of movement. This provides a further advantage for this embodiment of the invention, namely, electrostatic charges of the test material 1, in each case, are withdrawn prior to the moisture measurement by the parts of the electrodes 5 at zero potential extending transverse to the direction of movement. In this way there is realized a further reduction in the disturbance of the measurement results owing to static disturbance voltages at the test material.

A further advantageous construction of a part of the electrode arrangement has been illustrated in FIG. 4. In this case the electrode arrangement E'' is characterized by the fact that the cylinder 3' arranged above the test material 1, consists of individual disks or plates. There are thus formed ring-shaped electrodes. Hence, in the lengthwise direction of the cylinder 3' there altenately follow one another a positive potential carrying disk 4', an insulating 32', a zero potential carrying disk 5', an insulating disk 32', a negative potential carrying disk 6', an insulating disk 32' and so forth. Also in this case by virtue of the electrode 5' which is at zero potential and located between the electrodes 4' and 6' there is brought about a removal of damaging electrostatic charges.

FIG. 5 is a sectional view through an apparatus according to FIG. 2, wherein an electrical field 28 extending in the transverse direction of the test material 1 and two electrical fields 30 and 31 extending in the lengthwise direction of the test material have been shown. In this regard compare also FIG. 1.

Figure 6:
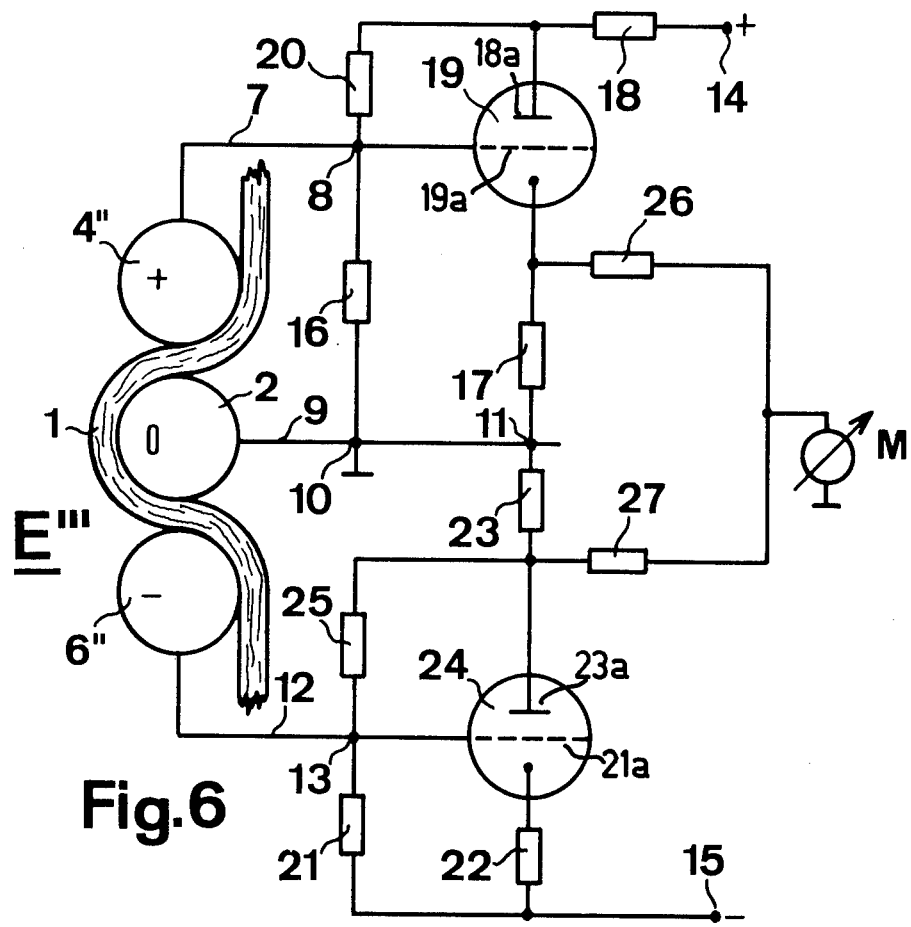
FIG. 6 illustrates a further construction of the present invention.

FIG. 6 illustrates a further advantageous construction of the invention wherein the electrode arrangement E''' consists of a cylindrical-shaped electrode 4'' which is at positive potential, a likewise cylindrical-shaped ground electrode 2 which is at zero potential, and a likewise cylindrical-shaped electrode 6'' which is at negative potential. The test material 1 is introduced between the ground electrode 2 and the electrodes 4'' and 6''. Both of the electrodes 4'' and 6'' are thus not arranged at the same cylinder, as such was the case for the electrodes 4 and 6 of FIG. 2, rather there are separate cylinders, however with parallelly extending axes. The connection of the electrode arrangement E''' with the amplifier arrangement V corresponds to that of FIG. 1.

With the embodiment of FIG. 6 there is realized the previously mentioned advantage of extensive immunity to disturbances from noise or hum, due to the push-pull arrangement of the electrode arrangement and the construction of the amplifier arrangement V explained on the basis of the showing of FIG. 1. On the other hand, the removal of electrostatic charges from the test material 1 prior to the moisture measurement, as such is realized with an electrode arrangement for instance of the type shown in FIG. 2, is here not the case. In certain instances, and especially when the amplifier arrangement V is constructed as a tube amplifier, there can nonetheless be realized satisfactory results.

Figure 7:
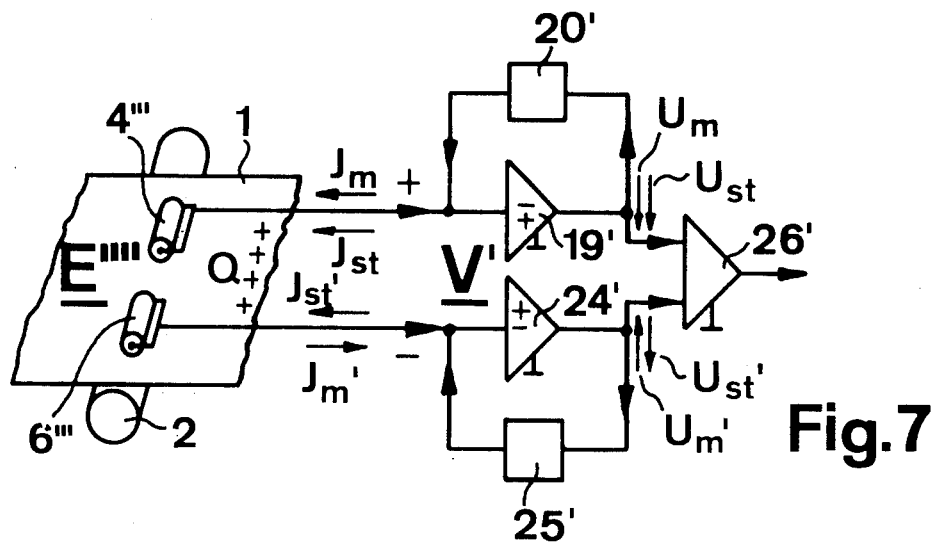
FIG. 7 illustrates a still further construction of the invention.

Finally, FIG. 7 illustrates a further advantageous exemplary embodiment of the invention. The electrode arrangement E'''' is here manifested by the features that also in this case the respective positive and negative potential carrying electrodes $4''''$ and $6'''$ are not arranged upon a cylinder, rather upon two separate cylinders, yet such are arranged with coinciding axial directions.

The amplifier arrangement V' according to the embodiment illustrated in FIG. 7 is designed a semi-conductor circuit. It operates however analogous to the example explained on the basis of FIG. 1. Instead of the tubes 19 and 24 there are here provided integrated amplifiers 19' and 24' with associated feedback networks 20' and 25' and the formation of the output signal takes place by means of a differential amplifier 26' at which there is subsequently connected the measuring element M. There are preferably used as the amplifiers 19' and 24' integrated amplifiers having field-effect transistor input. Such amplifiers and their use are well known so that no further discussion is here believed to be necessary.

With the arrangement of FIG. 7 there appears a measuring current $J_m$ in the indicated direction. By means of for instance a positive static charge Q at the test material 1 there is produced a disturbance current $J_{st}$ having the indicated direction.

Owing to the currents $J_m$ and $J_{st}$ flowing in the input circuit of the amplifier 19' there appear at its output the voltage charges $U_m$ and $U_{st}$, both with the same polarity. Owing to the currents $J_m$ and $J_{st}$ flowing in the input circuit of the amplifier 24' there appear at its output the voltage changes $U_m'$ and $U_{st}'$.

The voltage changes $U_m$ and $U_m'$ are directed opposite, whereas the voltage changes $U_{st}$ and $U_{st}'$ are similarly directed.

Therefore, the differential amplifier 26' produces an output signal which corresponds to the difference of the voltage changes $U_m$ to $U_m'$ and $U_{st}$ to $U_{st}'$, wherein the latter, due to their same magnitude and direction, are eliminated.

While there are shown and described present preferred embodiments of the invention, it is to be distinctly understood that the invention is not limited thereto, but may be otherwise variously embodied and practiced within the scope of the following claims. Accordingly,

What is claimed is:

1. A method for measuring the moisture content of flat textile structures, especially textile webs, comprising the steps of: feeding a textile structure along a predetermined path of travel, carrying out a moisture measuring operation, deriving by virtue of the measuring operation useful signal components of the same polarity dependent upon the conductance of the test material, and disturbance signal components of opposed polarity dependent upon external voltages, adding the useful signal components to form a measurement value, and adding the disturbance signal components which by virtue of their opposed polarity at least approximately eliminate one another.

2. The method as defined in claim 1, further including the step of removing electrical charges from the test structure prior to electrodes serving for the moisture measurement contacting the test structure.

3. An apparatus for measuring the moisture of flat textile structures, especially textile webs, comprising an electrode arrangement for contacting the flat textile structure defining a test material, the electrode arrangement comprising at least one ground electrode, at least one electrode at positive potential, at least one electrode at negative potential, an amplifier arrangement having a first input and a second input, said amplifier arrangement including two direct-current series connected partial amplifiers, the positive potential carrying electrode being connected with the first input of the amplifier arrangement and the negative potential carrying electrode being connected with the second input of the amplifier arrangement.

4. The apparatus as defined in claim 3, wherein the electrode arrangement comprises a substantially cylindrical insulating body having a jacket surface at which there are present the positive potential carrying electrode, the ground potential carrying electrode and the negative potential carrying electrode.

5. The apparatus as defined in claim 4, wherein the electrodes at positive and negative potentials have a substantially comb-like configuration which are offset with respect to one another and directed towards one another.

6. The apparatus as defined in claim 5, including a meander-shaped ground electrode arranged between combs of the comb-shaped electrodes.

7. The apparatus as defined in claim 3, wherein the electrodes define substantially ring-shaped electrodes.

8. The apparatus as defined in claim 7, wherein the ring-shaped electrodes are formed by disks of substantially the same diameter, and insulating disks for electrically insulating from one another said disks of substantially the same diameter.

9. The apparatus as defined in claim 3, wherein the electrode arrangement is constructed such that electrical fields are formed which extend transversely and lengthwise of the test material, and the dimensions of the electrode arrangement are chosen such that there is realized an at least approximate compensation of the influence of the thickness of the test material upon the moisture measurement result.

10. The apparatus as defined in claim 3, wherein the electrode arrangement comprises a respective cylinder of conductive material for each said electrode carrying the positive potential and the negative potential and the electrode carrying the ground potential, all of said cylinders being arranged at least approximately axially parallel to one another.

11. The apparatus as defined in claim 3, wherein the respective electrodes at positive and negative potentials are arranged at least approximately along a single axis.

* * * * *